(12) United States Patent
Kang

(10) Patent No.: US 11,660,463 B2
(45) Date of Patent: May 30, 2023

(54) VAGINAL TREATMENT DEVICE USING LEDS, HIGH-FREQUENCY WAVES, AND EMS

(71) Applicant: Sun-Young Kang, Seoul (KR)

(72) Inventor: Sun-Young Kang, Seoul (KR)

(*) Notice: Subject to any disclaimer, the term of this patent is extended or adjusted under 35 U.S.C. 154(b) by 167 days.

(21) Appl. No.: 17/197,113

(22) Filed: Mar. 10, 2021

(65) Prior Publication Data

US 2021/0283419 A1   Sep. 16, 2021

(30) Foreign Application Priority Data

Mar. 16, 2020   (KR) .................. 10-2020-0031713

(51) Int. Cl.
*A61N 5/06* (2006.01)
*A61N 1/05* (2006.01)

(52) U.S. Cl.
CPC .......... *A61N 5/0603* (2013.01); *A61N 1/0524* (2013.01); *A61N 5/0613* (2013.01); *A61N 2005/0611* (2013.01); *A61N 2005/0632* (2013.01); *A61N 2005/0644* (2013.01); *A61N 2005/0663* (2013.01)

(58) Field of Classification Search
CPC .......... A61N 1/0524; A61N 2005/0611; A61N 2005/0644; A61N 5/0603
See application file for complete search history.

(56) References Cited

U.S. PATENT DOCUMENTS

| | | | |
|---|---|---|---|
| 4,785,828 A * | 11/1988 | Maurer | A61F 2/005 600/382 |
| 10,039,929 B1 * | 8/2018 | Schwarz | A61N 1/36007 |
| 2009/0319008 A1 * | 12/2009 | Mayer | A61N 5/0624 607/90 |
| 2011/0230931 A1 * | 9/2011 | Hagege | A61N 1/0524 607/41 |
| 2015/0133832 A1 * | 5/2015 | Courtion | A61H 19/40 601/18 |
| 2017/0209707 A1 * | 7/2017 | Casalino | A61N 1/06 |
| 2018/0296383 A1 * | 10/2018 | Blanche | A61H 19/44 |
| 2022/0273919 A1 * | 9/2022 | Kraft | A61N 5/0603 |

FOREIGN PATENT DOCUMENTS

| | | | | |
|---|---|---|---|---|
| KR | 101449542 B1 * | 10/2014 | | A61N 5/06 |
| KR | 2018113824 A * | 10/2018 | | A61F 7/12 |
| KR | 101958845 B1 * | 3/2019 | | A61N 5/06 |
| KR | 20200039996 A1 * | 4/2020 | | A61N 5/06 |
| WO | WO-2015059120 A1 * | 4/2015 | | A61N 1/0524 |
| WO | WO-2017221277 A1 * | 12/2017 | | A61N 1/05 |

* cited by examiner

*Primary Examiner* — Nathan J Jenness
(74) *Attorney, Agent, or Firm* — Stein IP, LLC

(57) ABSTRACT

The present disclosure relates to a vaginal treatment device using LEDs, high-frequency waves, and EMS, the vaginal treatment device including: a main body part configured to be inserted into a vagina and having one or more LED irradiation units configured to irradiate an interior of the vagina with light, and electrode units configured to transfer radio frequency (RF) energy or electro muscular stimulation (EMS) energy into the vagina; a handle part embedded with a battery and having a power source member connected to one end of the main body part and configured to control transmission and reception to/from the LED irradiation units or the electrode units; and a housing part electrically connected to the handle part and configured to charge the battery.

16 Claims, 21 Drawing Sheets

20

VAGINAL TREATMENT DEVICE USING LEDS, HIGH-FREQUENCY WAVES, AND EMS

CROSS-REFERENCE TO RELATED APPLICATION

This application claims priority to and the benefit of Korean Patent Application No. 10-2020-0031713 filed in the Korean Intellectual Property Office on Mar. 16, 2020, the entire contents of which are incorporated herein by reference.

TECHNICAL FIELD

The present disclosure relates to a vaginal treatment device using LEDs, high-frequency waves, and EMS, and more particularly, to a vaginal treatment device using LEDs, high-frequency waves, and EMS, which may be used in a wireless manner and may selectively use LEDs or high-frequency energy and low-frequency energy.

BACKGROUND ART

Elasticity of an inner wall of a vaginal canal, which is a woman's genital organ, decreases due to childbirth or aging, and particularly, the inner wall of the vaginal canal is rapidly relaxed. The relaxed inner wall of the vaginal canal recovers to some extent after childbirth. However, the relaxed inner wall of the vaginal canal is rarely restored to have elasticity before childbirth, which causes urinary incontinence.

In general, about 30 to 40% of adult women statistically suffer from the urinary incontinence. The urinary incontinence is suffered by middle-aged women typically due to reasons such as pregnancy, childbirth, menopause, aging, obesity. The urinary incontinence refers to a disease in which urine is unconsciously released in a situation in which force is applied to an abdomen while coughing, sneezing, and walking.

It has been known that the urinary incontinence is caused by a loosened pelvis muscle or a decrease in muscular strength of a urethral sphincter caused by menopause, and most patients suffer from difficulty in daily life. The urinary incontinence has been treated by various treatment methods (medicine treatment using anticholinergic drugs, pelvic muscle exercise, electrical stimulation treatment, and surgical treatment using a tension-free vaginal tape (TVT)), and other treatment methods using separate treatment devices are performed to treat the urinary incontinence.

Meanwhile, in the case of technologies in the related art for treating the urinary incontinence, a patient may typically increase muscular strength of the relaxed urethral sphincter by inserting a device into the patient's vagina (hereinafter, referred to as a "body part") and then taking the patient's own contraction and relaxation exercise of the body part. Therefore, the patient may inhibit excretion of urine caused by the urinary incontinence.

However, the device in the related art used to treat the urinary incontinence is disadvantageous in that a sensitive body part is often injured by an edge portion of a quadrangular body of the device, which aggravates the urinary incontinence. In addition, the device in the related art has a problem in that a sharp portion of the device is exposed in a process of using the device for treating the urinary incontinence, which causes serious damage to the body part. In addition, there is a problem in that the patient feels embarrassed because the shape of the device is exposed when the device is used.

RELATED ART DOCUMENT

Korean Utility Model Registration No. 20-0437906 (Dec. 28, 2007)

SUMMARY OF THE INVENTION

An object of the present disclosure is to provide a vaginal treatment device using LEDs, high-frequency waves, and EMS, which may increase decreased muscular strength of vaginal inner wall by selectively using LEDs, high-frequency energy, or low-frequency energy.

Another object of the present disclosure is to provide a vaginal treatment device using LEDs, high-frequency waves, and EMS, which may be easily used in a wireless manner and have improved durability.

Still another object of the present disclosure is to provide a vaginal treatment device using LEDs, high-frequency waves, and EMS, which is inserted into a vagina of a woman and irradiates an interior of the vagina with blue light or red light, thereby enhancing and restoring vaginal muscles.

One aspect of the present disclosure provides a vaginal treatment device using LEDs, high-frequency waves, and EMS, the vaginal treatment device including: a main body part configured to be inserted into a vagina and having one or more LED irradiation units configured to irradiate an interior of the vagina with light, and electrode units configured to transfer radio frequency (RF) energy or electro muscular stimulation (EMS) energy into the vagina; a handle part embedded with a battery and having a power source member connected to one end of the main body part and configured to control transmission and reception to/from the LED irradiation units or the electrode units; and a housing part electrically connected to the handle part and configured to charge the battery.

In one exemplary embodiment, the LED irradiation units may include first LED units comprising red-light LEDs, and second LED units comprising blue-light LEDs, and the first LED units, the electrode units, and the second LED units may be sequentially provided and aligned on the main body part.

In one exemplary embodiment, the main body part may extend in a first direction, the handle part may be provided on the main body part and may extend perpendicular to the first direction, and the first LED unit may be provided adjacent to the handle part.

In one exemplary embodiment, the first LED unit may be spaced apart from one end of the main body part by 25 mm to 35 mm, and the second LED unit may be spaced apart from one end of the main body part by 55 mm to 65 mm.

In one exemplary embodiment, the main body part may further include a silicone cover made of silicone and provided to cover at least some of the LED irradiation units, the silicone cover may cover the LED irradiation units, and the electrode units may be provided on an outer surface of the silicone cover.

In one exemplary embodiment, the first LED unit may emit light in a red wavelength band of 575 nm to 750 nm, and the second LED unit may emit light in a blue wavelength band of 405 nm to 520 nm.

In one exemplary embodiment, the electrode unit may be spaced apart from one end of the main body part by 40 mm to 50 mm, the RF energy may have an output power of 10

W to 20 W, an output voltage of 150 Vpp to 200 Vpp, a frequency of 0.8 MHz to 1.5 MHz, and a temperature of 30° C. to 48° C., and the EMS energy may have an output voltage of 20 V to 30 V, a maximum current of 10 mA to 30 mA, a pulse width of 20 us to 500 us, and a frequency of 2 Hz to 500 Hz.

In one exemplary embodiment, the housing part may include: a bottom housing having an internal space for receiving the main body part and at least a part of the handle part, and a top housing provided to cover one side of the bottom housing and configured to cover the handle part.

In one exemplary embodiment, the bottom housing further may include: a USB PCB terminal configured to be supplied with power from the outside; and a terminal plate configured to be electrically connected to the handle part, in which the handle part may have terminal blocks configured to be electrically connected to the terminal plate, in which the internal space may include: a lower receiving portion provided to correspond to the main body part and disposed at a lower side of the housing part so that the main body part is inserted into the lower receiving portion; and an upper receiving portion connected to an upper side of the lower receiving portion and configured to receive at least a part of the handle part, in which one part of the handle part may be inserted into the upper receiving portion, and the other part of the handle part may protrude upward from the bottom housing, in which the top housing may be provided in a dome shape so as to surround the handle part and cover the handle part protruding upward from the bottom housing, and in which one or more reinforcing ribs may be provided on an inner surface of the top housing so as to reinforce strength of the top housing.

In one exemplary embodiment, the bottom housing may further have planar heating elements provided at positions corresponding to an outer circumferential edge of the internal space in order to dry or sterilize the main body part received in the internal space, and in which the planar heating element may be made by attaching coating paper to two surfaces of sun-paper heating sheets, which are made of carbon fiber heating paper, between the sun-paper heating sheets and configured to emit heat by supplying power to two electrodes.

In one exemplary embodiment, the terminal plate may be provided at an outer circumferential edge of the upper receiving portion, at least a part of an outer surface of the handle part may be seated at the outer circumferential edge of the upper receiving portion, and the terminal blocks of the handle part and the terminal plate may be connected to one another.

In one exemplary embodiment, a first protruding key portion and a second protruding key portion may be provided on a lower surface of the handle part so as to protrude from the lower surface of the handle part and disposed at positions corresponding to the outer circumferential edge of the upper receiving portion, in which the terminal blocks may include a first terminal block, which is a (+) terminal, and a second terminal block, which is a (−) terminal, and the first terminal block and the second terminal block may be provided to be spaced apart from each other, in which the first protruding key portion may be provided adjacent to the first terminal block, and the second protruding key portion may be provided adjacent to the second terminal block, and in which first and second key groove portions may be provided in the upper receiving portion and formed to be concave inward corresponding to the first and second protruding key portions so that the first and second protruding key portions are inserted into the first and second key groove portions, respectively.

In one exemplary embodiment, the first protruding key portion may be provided in a cylindrical shape having a circular transverse section, and the second protruding key portion may be provided in a plate shape having a "-" shaped transverse section.

In one exemplary embodiment, the electrode unit may further have a human body sensing function or a contact temperature sensing function.

In one exemplary embodiment, the main body part may further have human body detecting sensors, in which when power may be applied through the handle part, the LED irradiation units or the electrode units may be operated after the sensors detect a human body, in which the LED irradiation units may include: the first LED units including red-light LEDs; and the second LED units including blue-light LEDs, in which the first LED units, the electrode units, and the second LED units may be sequentially disposed on the main body part, and in which the sensors may include: first sensors provided between the first LED units and the electrode units to control operations of the first LED units; second sensors provided between the electrode units and the second LED units to control operations of the electrode units; and third sensors provided between the second LED units and an end of the main body part to control operations of the second LED units.

In one exemplary embodiment, the main body part and the handle part may be integrally provided, in which the battery embedded in the handle part may operate the LED irradiation units and the electrode units of the main body part in a wireless manner, in which the main body part may extend from one end in a first direction and may have an end, in which the handle part may be connected to one end of the main body part so as to be perpendicular to one end of the main body part, and cross sections of the main body part and the handle part may be connected in a T shape, in which the main body part may have a cap-shaped silicone cover provided at the end of the main body part and configured to cover the LED irradiation units of the main body part, in which the LED irradiation units may be mounted on the body, in which the silicone cover may be provided in a cone shape, and an interior at an end of the silicone cover may be provided to be in contact with the lower end of the body, and in which an outer surface of the silicone cover may be rounded without edge.

In one exemplary embodiment, the LED irradiation units may include: the first LED units including red-light LEDs; and the second LED units including blue-light LEDs, in which the first LED units, the electrode units, and the second LED units may be sequentially provided and aligned at one end of the main body part, in which the first LED units and the second LED units may be provided inside the silicone cover and covered by the silicone cover, in which the plurality of electrode units may be provided on the outer surface of the silicone cover so as to have a quadrangular cross section, and in which an outer surface of the electrode unit may be rounded in the first direction.

In one exemplary embodiment, the six electrode units may be disposed in a direction perpendicular to the first direction so as to surround the main body part and provided to be spaced apart from one another, and the handle part may include: a power button configured to turn on/off a power source of the battery; and a level button configured to control intensity of one or more of the first LED units, the electrode units, and the second LED units.

According to the present disclosure described above, it is possible to provide the vaginal treatment device using LEDs, high-frequency waves, and EMS, in which the portion to be inserted into the vagina is provided to correspond to the interior of the vagina, and light, a high-frequency wave, or low-frequency energy is controlled and emitted depending on the position of the vagina, thereby more effectively enhancing and restoring the muscles in the vagina.

In addition, according to the present disclosure, it is possible to provide the vaginal treatment device using LEDs, high-frequency waves, and EMS, which may be used in a wireless manner and have the portion that protrudes outward from the vagina but is naturally covered in the human body, and as a result, it is possible to reduce discomfort during use and improve portability.

In addition, according to the present disclosure, it is possible to provide the vaginal treatment device using LEDs, high-frequency waves, and EMS, in which the intensity of the light and the intensity of the high-frequency waves and the low-frequency waves may be easily controlled from the outside, and the human body detecting sensors are used to generate and control light, high-frequency waves, low-frequency waves, or the like at a particular site in the vagina, thereby further improving safety.

DETAILED DESCRIPTION

Figure 1:
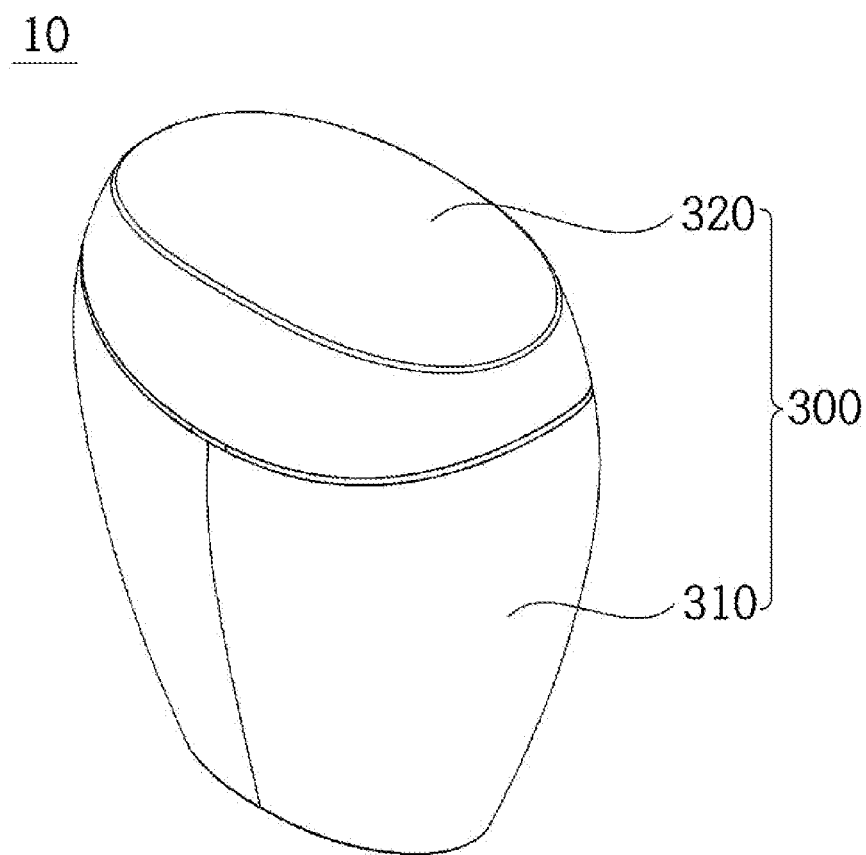
FIG. 1 is a perspective view of a vaginal treatment device according to an exemplary embodiment of the present disclosure.

Other detailed matters of the exemplary embodiment are included in the detailed description and the drawings.

Advantages and features of the present disclosure and methods of achieving the advantages and features will be clear with reference to exemplary embodiments described in detail below together with the accompanying drawings. However, the present disclosure is not limited to the exemplary embodiments disclosed herein but will be implemented in various forms. In the following description, when one constituent element is referred to as being "connected to" another constituent element, one constituent element can be "directly connected to" the other constituent element, and one constituent element can also be "connected to" the other element with other elements therebetween. A part irrelevant to the description will be omitted in the drawings in order to clearly describe the present disclosure, and similar constituent elements will be designated by similar reference numerals throughout the specification.

Hereinafter, the present disclosure will be described with reference to the accompanying drawings.

Figure 2:
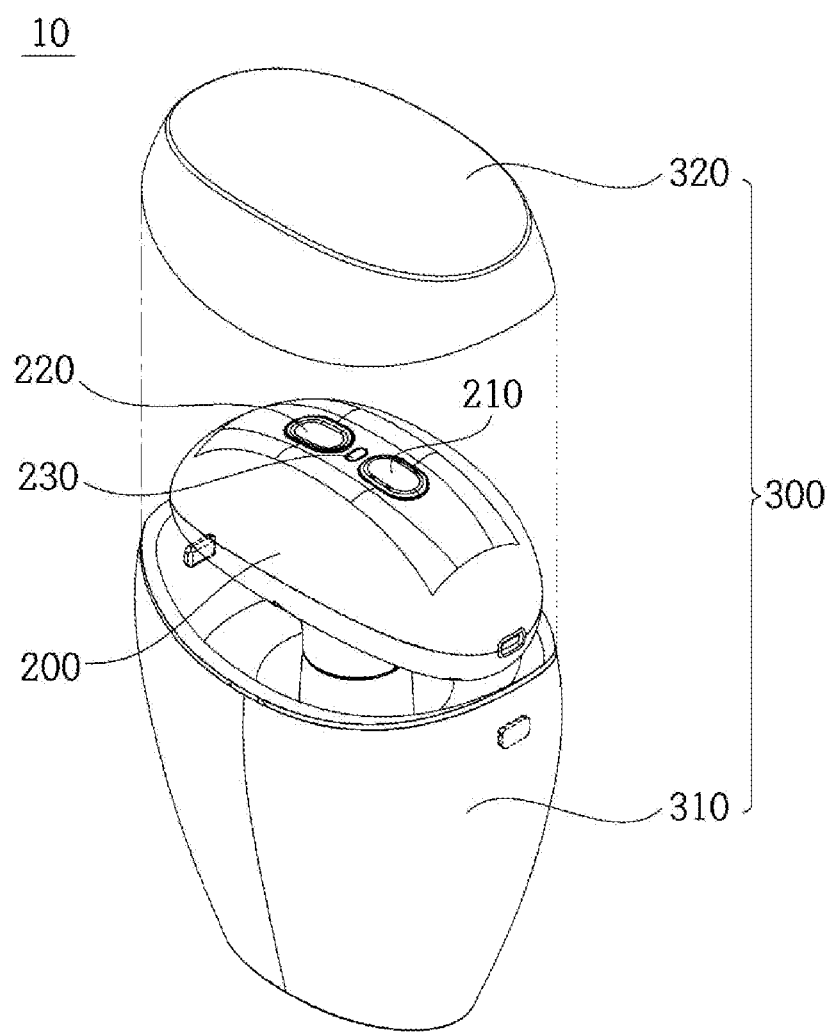
FIG. 2 is an exploded perspective view of FIG. 1.
Figure 3A:
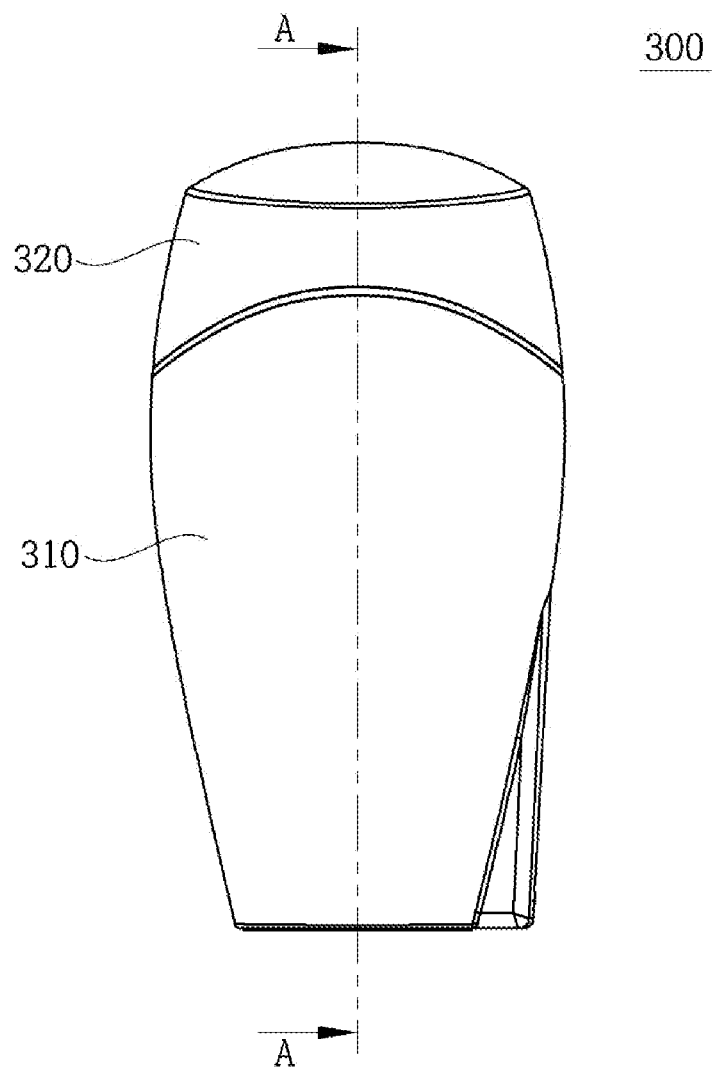
FIGS. 3A to 3D are views illustrating lateral sides and cross sections of a housing part illustrated in FIG. 1.
Figure 3B:
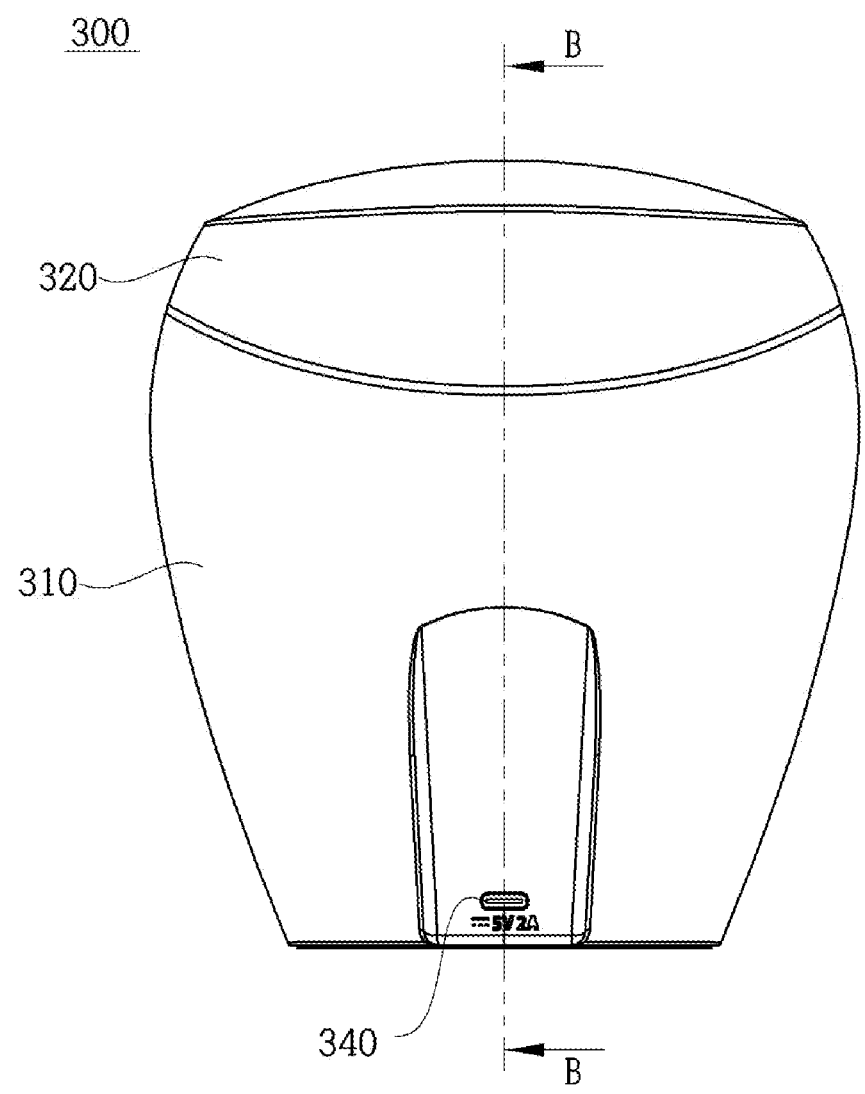
Figure 3C:
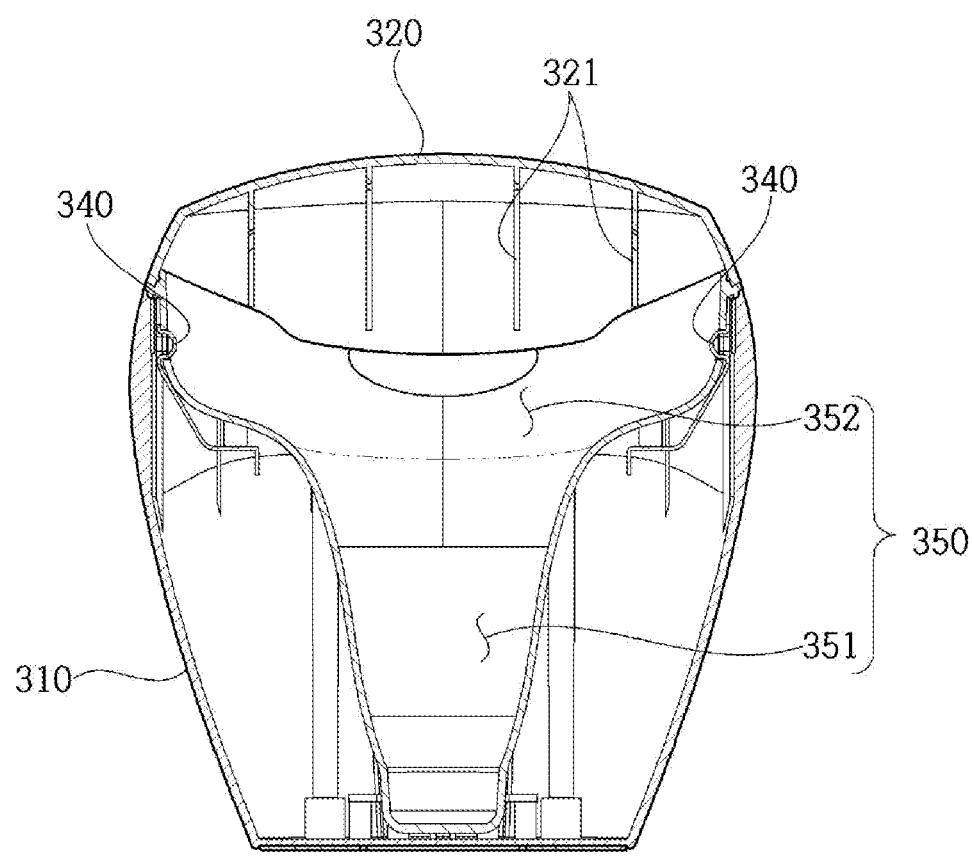
Figure 3D:
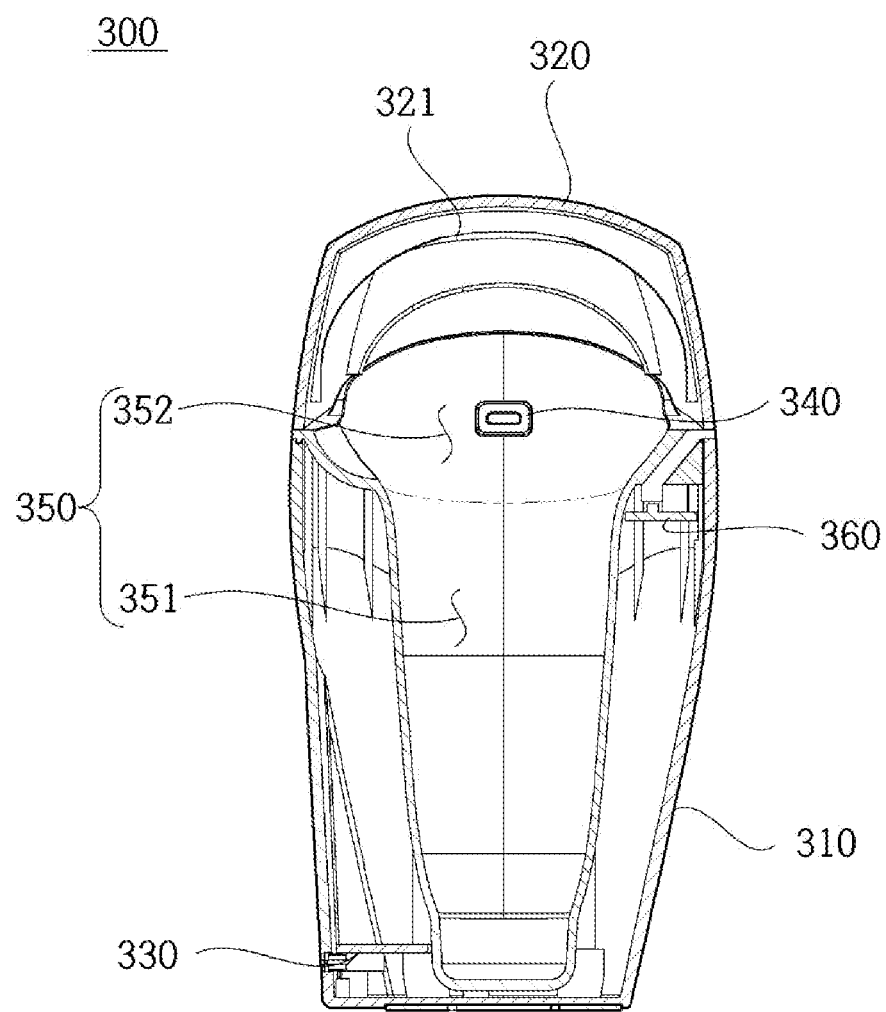
Figure 4:
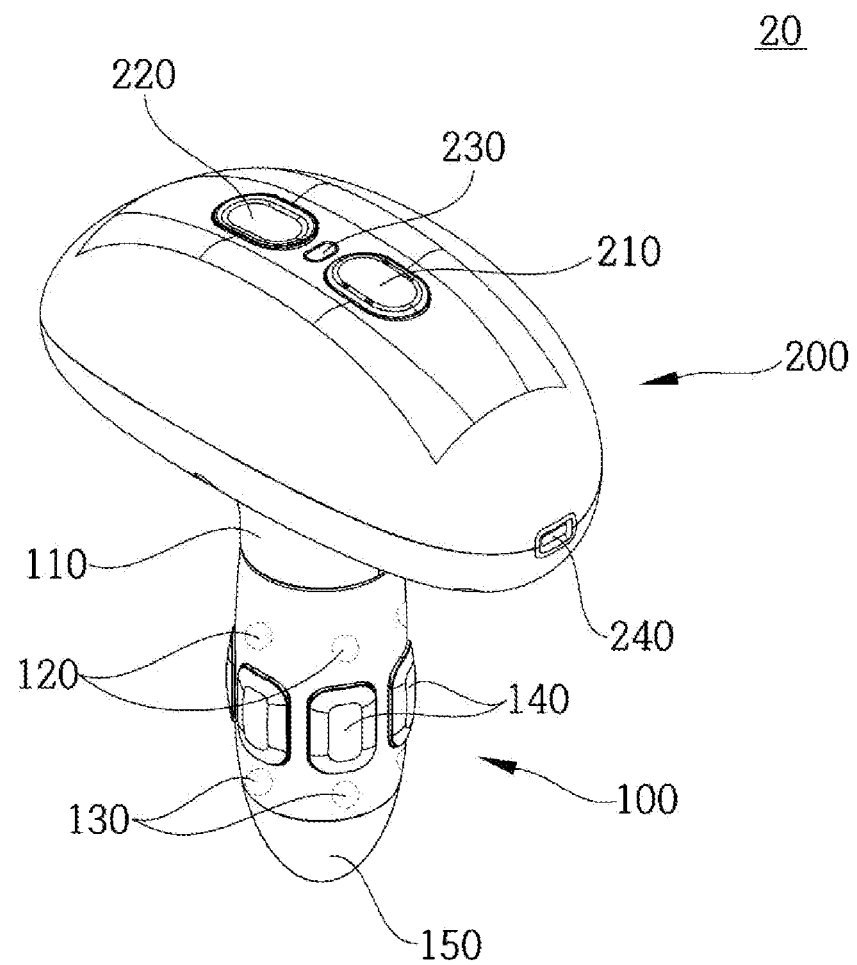
FIG. 4 is a perspective view of a hand piece including a main body part and a handle part.
Figure 5A:
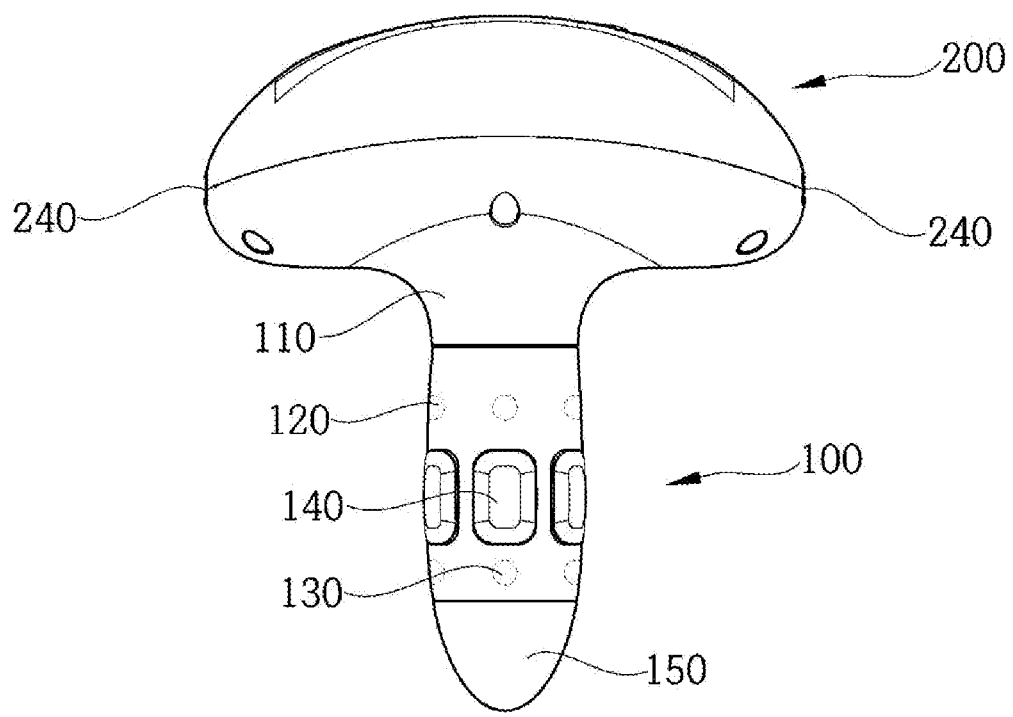
FIGS. 5A and 5B are views illustrating a front side and a lower side of FIG. 4.
Figure 5B:
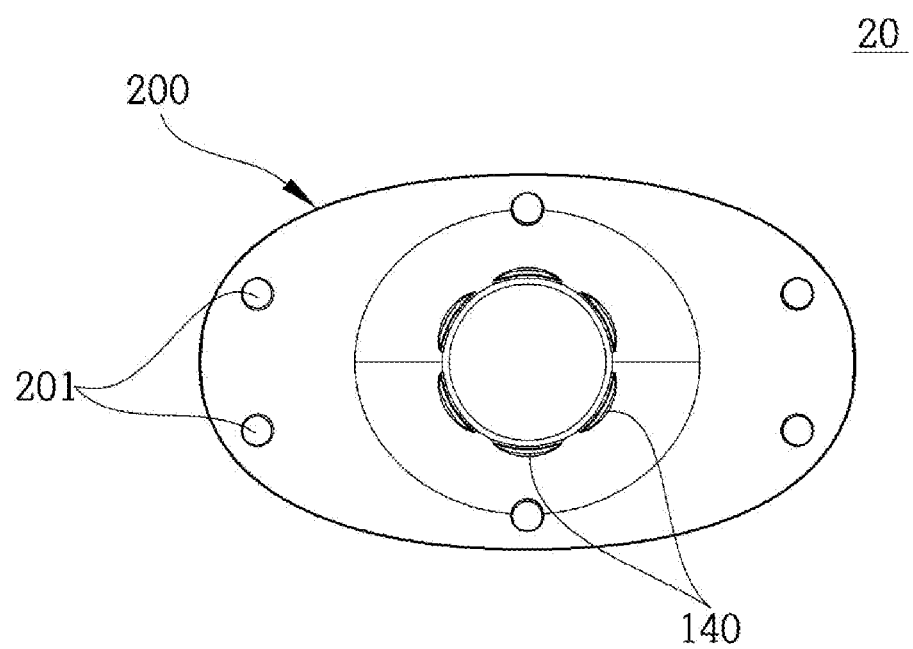
Figure 6:
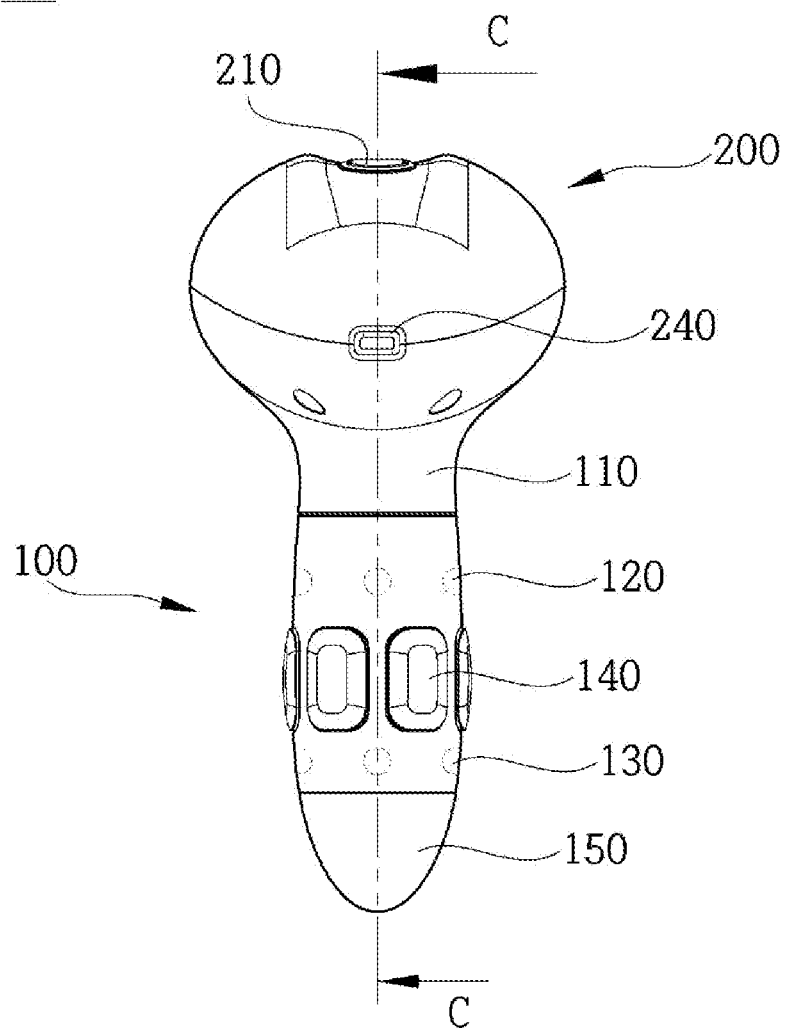
FIG. 6 is a view illustrating a lateral side of FIG. 4.
Figure 7:
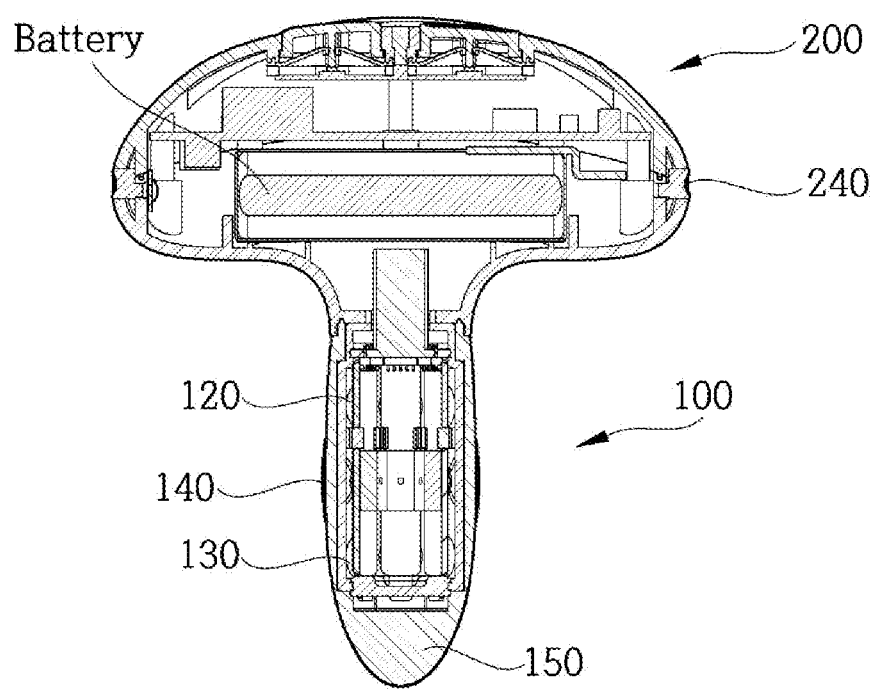
FIG. 7 is a view illustrating a cross section of FIG. 6.
Figure 8:
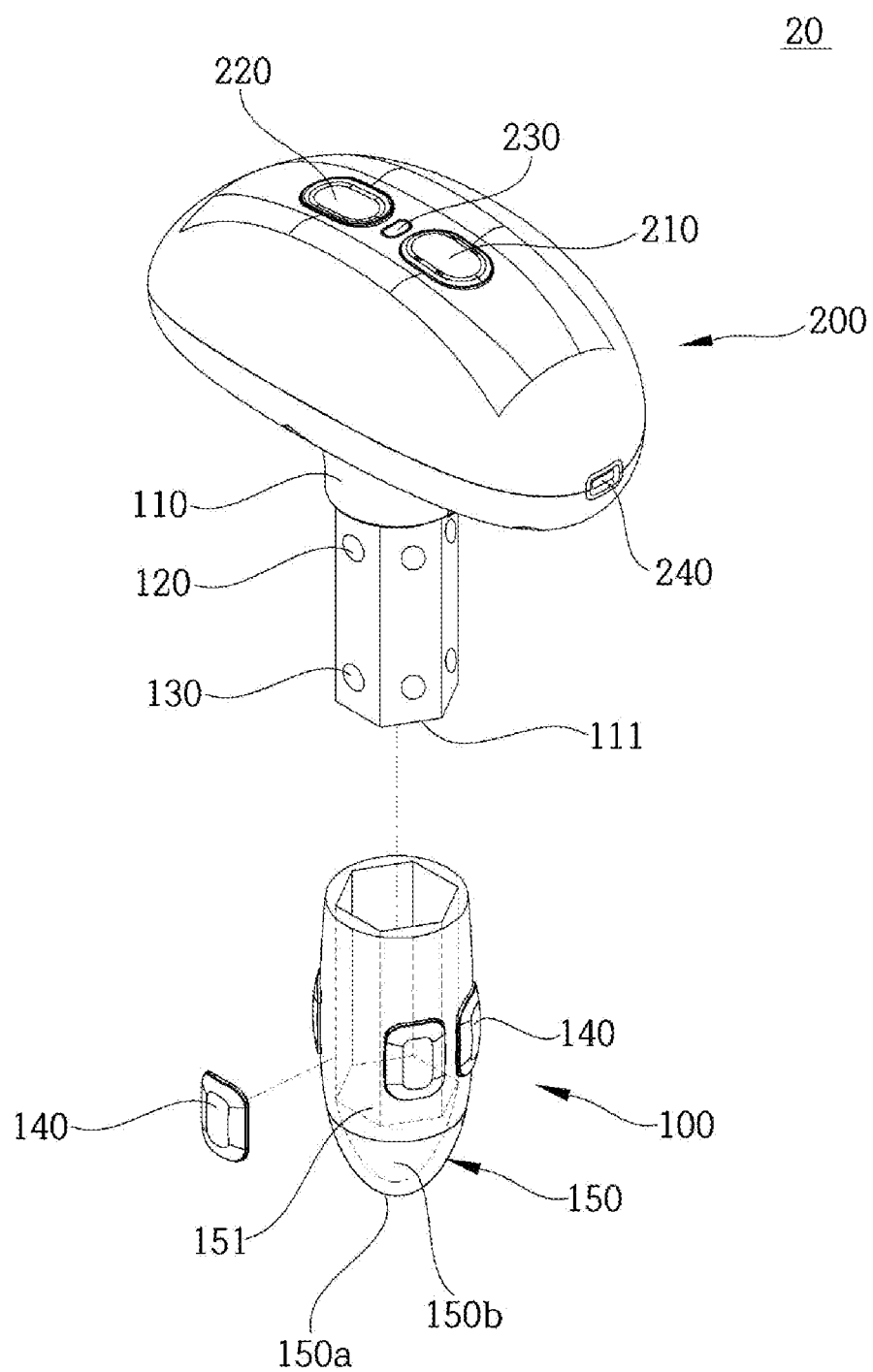
FIG. 8 is an exploded perspective view of FIG. 4.

FIG. 1 is a perspective view of a vaginal treatment device according to an exemplary embodiment of the present disclosure. FIG. 2 is an exploded perspective view of FIG. 1. FIGS. 3A to 3D are views illustrating lateral sides and cross sections of a housing part illustrated in FIG. 1. FIG. 4 is a perspective view of a hand piece including a main body part and a handle part. FIGS. 5A and 5B are views illustrating a front side and a lower side of FIG. 4. FIG. 6 is a view illustrating a lateral side of FIG. 4. FIG. 7 is a view illustrating a cross section of FIG. 6. FIG. 8 is an exploded perspective view of FIG. 4.

Figure 9:
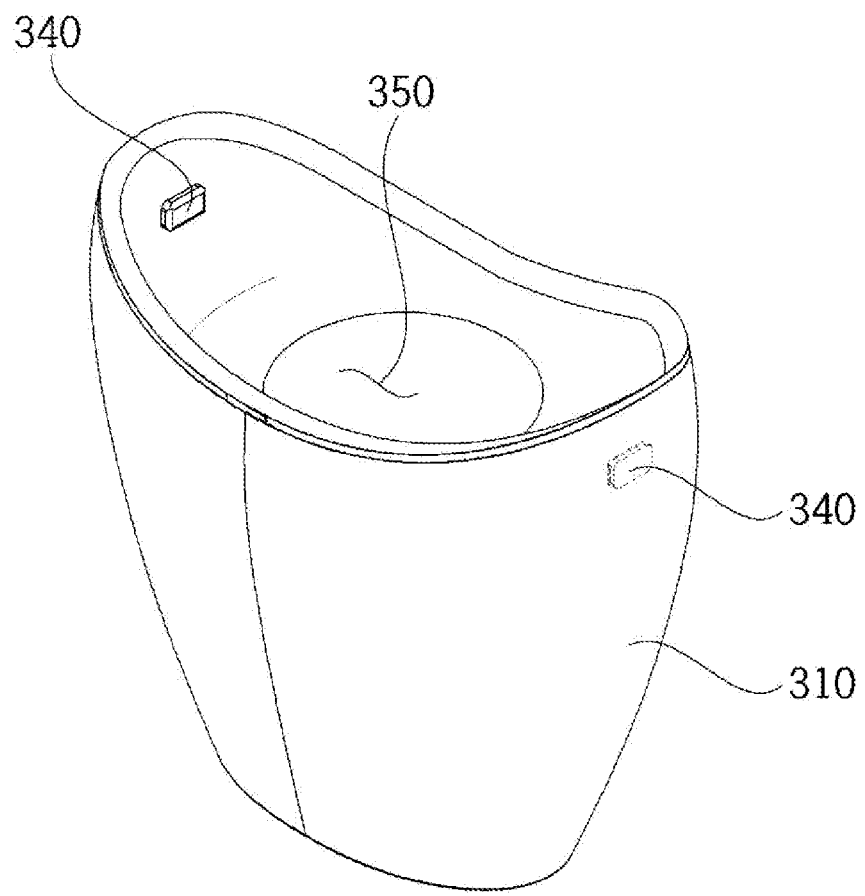
FIGS. 9 and 10 are views illustrating a bottom housing.
Figure 10:
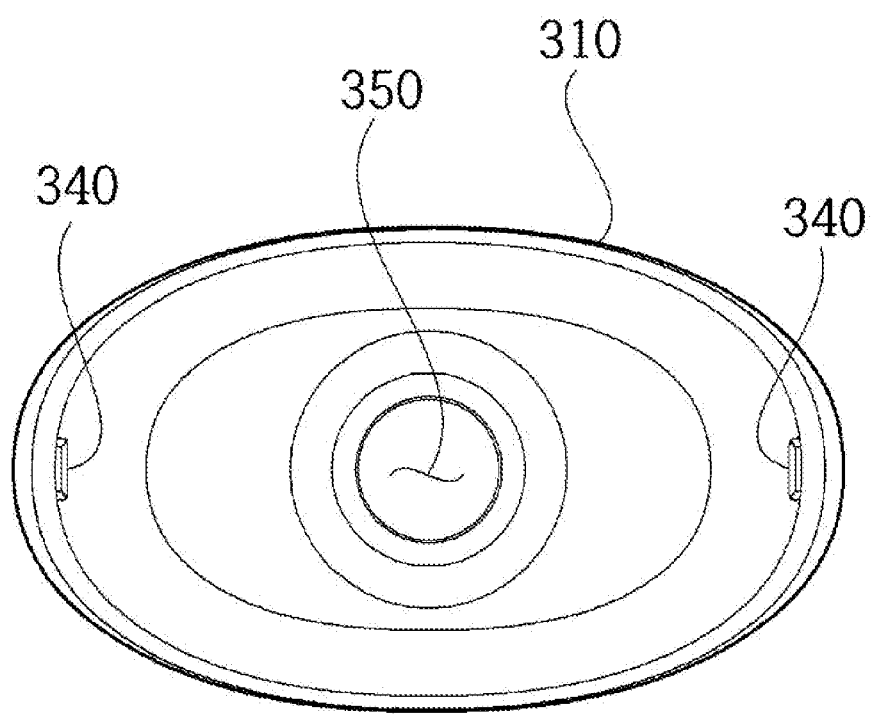

FIGS. 9 and 10 are views illustrating a bottom housing.

An exemplary embodiment of the present disclosure relates to a vaginal treatment device 10 using LEDs, high-frequency waves, and EMS 10, and the vaginal treatment device 10 includes a main body part 100 configured to be inserted into a vagina and having one or more LED irradiation units 120 and 130 configured to irradiate an interior of the vagina with light, and electrode units 140 configured to transfer radio frequency (RF) energy or electro muscular stimulation (EMS) energy into the vagina; a handle part 200 embedded with a battery and having a power source member connected to one end of the main body part 100 and configured to control transmission and reception of power to/from the LED irradiation units 120 and 130 or the electrode units 140; and a housing part 300 electrically connected to the handle part 20 and configured to charge the battery.

The vaginal treatment device 10 according to the present exemplary embodiment may include a hand piece 20 having the main body part 100 configured to be inserted into a woman's vagina, and the handle part 200 integrally connected to one side of the main body part 100; and a housing part 300 configured to store the hand piece 20.

The main body part 100 and the handle part 200, which constitute the hand piece 20, may be integrally provided and operated in a wireless manner by means of the battery embedded in the handle part 200. Therefore, after the main body part 100 is inserted into a woman's vagina, the LED irradiation units 120 and 130 and the electrode units 140 of the main body part 100 may be operated by power from the battery embedded in the handle part 200 to transfer the light, the RF energy, and the EMS energy into the vagina.

When the hand piece 20 is inserted and stored in the housing part 300, the battery in the handle part 200 may be charged by the housing part 300. The handle part 200 is electrically connected to the housing part 300 and may charge the battery with power supplied from the outside through the housing part 300.

The vaginal treatment device 10 according to the present exemplary embodiment may treat the interior of the vagina using the hand piece 20 provided to be separable from the housing part 300 and configured to operate in a wireless manner, as a result, a user may more conveniently use the hand piece 20 in comparison with a hand piece connected in a wired manner in the related art.

In addition, because the vaginal treatment device 10 according to the present exemplary embodiment is not exposed to the outside after being inserted into the interior of the vagina, the user may use the vaginal treatment device 10 in a state in which others cannot know the use of the vaginal treatment device 10. As a result, the user may more freely use the vaginal treatment device 10 without limitation of place.

The main body part 100 extends from one end in a first direction and has an end, the handle part 200 is connected to one end of the main body part 100 so as to be perpendicular to the first direction, and cross sections of the main body part 100 and the handle part 200 may be connected in a T shape. The main body part 100 may have a cap-shaped silicone cover 150 provided at the end of the main body part 100 and configured to cover the LED irradiation units 120 and 130 of the main body part 100.

The main body part 100 may have a body 110 integrally connected to the handle part 200 and having a lower end 111 having a flat surface, and the silicone cover 150 configured to cover the lower end 111 of the body 110. The LED irradiation units 120 and 130 are mounted on the body 110, the silicone cover 150 is provided in a cone shape, and an interior at the end of the silicone cover 150 may be provided to be in contact with the lower end 111 of the body 110. An outer surface of the silicone cover 150 may be rounded without edge. The one or more electrode units 140 are provided on the outer surface of the silicone cover 150, and the electrode unit 140 may be mounted on the body 110 by passing through the silicone cover 150.

The body 110, which constitutes the main body part 100, may extend in a long column shape in the first direction. An upper end of the body 110 is connected to a lateral surface of the handle part 200. The lower end 111 of the body 110 has a flat surface, and a transverse section of the lower end 110 of the body 110 may have an approximately hexagonal shape. The body 110 may have an approximately octahedral shape having six lateral surfaces. The LED irradiation units 120 and 130 and the electrode units 120 are provided on the six lateral surfaces of the body 110, one for each lateral surface, such that the positions of the LED irradiation units 120 and 130 and the electrode units 120 may be guided and locked. In addition, the silicone cover 150 having elasticity is provided on an outer surface of the body 110. With the silicone cover 150 covering the body 110, the entire main body part 100 may have a curved outer surface without edge.

The LED irradiation units 120 and 130 include first LED units 120 including red-light LEDs, and second LED units 130 including blue-light LEDs. The first LED units 120, the electrode units 140, and the second LED units 130 may be sequentially provided and aligned at one end of the main body part 100. For example, the first LED units 120 may be provided adjacent to the handle part 200, the second LED units 130 may be provided to be spaced apart from the first LED units 120 at predetermined intervals and aligned in parallel with one another, and the electrode units 140 may be provided between the first LED units 120 and the second LED units 130.

The first LED units 120 and the second LED units 130 are provided inside the silicone cover 150 and covered by the silicone cover 150. The plurality of electrode units 140 may be provided on the outer surface of the silicone cover 150 and each may have a quadrangular cross section. An outer surface of the electrode unit 140 may be rounded in the first direction. For example, the electrode unit 140 has a metal plate shape and is mounted on the outer surface of the silicone cover 150. The overall shape of the electrode unit 140 corresponds to the silicone cover 150 provided in the form of a cone, such that a front surface of the electrode unit 140 may not be a flat surface but may be a curved surface protruding outward. Since the shape of the electrode unit 140 corresponds to the shape of the silicone cover 150, damage to skin caused by the electrode unit 140 may be avoided when the main body part 100 is inserted into the vagina.

The first LED unit 120 may emit light in a red wavelength band of 575 nm to 750 nm, and the second LED unit 130 may emit light in a blue wavelength band of 405 nm to 520 nm. Specifically, six LEDs may be provided as the first LED units 120, and six LEDs may be provided as the second LED units 130 at positions corresponding to the first LED units 120. Specifically, the blue wavelength band of the LED may be approximately 415 nm, and the red wavelength band of the LED may be approximately 630 nm.

The first LED units 120 may be spaced apart from one end of the main body part by 25 mm to 35 mm, and the second LED units 130 may be spaced apart from one end of the main body part by 55 mm to 65 mm. The first LED unit 120 and the second LED unit 130 are provided with wavelengths having different functions, respectively, and inserted into the vagina to perform the functions. For example, the first LED units 120 are provided on the main body part 100 so as to be adjacent to the handle part 200 and may sterilize a vaginal inlet portion during the use of the vaginal treatment device 10, thereby effectively preventing penetration of bacteria and the like. In addition, the second LED units 130 are provided adjacent to the end of the main body part 100 and used to control a degree of insertion of the main body part 100 into the vagina, such that the entirety of the interior of the vagina may be uniformly irradiated with the light, thereby effectively improving elasticity of the muscles in the vagina.

The six electrode units 140 may be disposed in a direction perpendicular to the first direction so as to surround the main body part 100 and provided to be spaced apart from one another. For example, the electrode units 160 are provided to be spaced apart from one another and each aligned with each of the six surfaces of the body 110 having the approximately six surfaces. The electrode units 160 are provided to surround the body 110 of the main body part 100.

The electrode units 140 are provided to be spaced apart from one end of the main body part 100 by 40 mm to 50 mm and may generate RF energy or EMS energy. The RF energy may have an output power of 10 W to 20 W, an output voltage of 150 Vpp to 200 Vpp, a frequency of 0.8 MHz to 1.5 MHz, and a temperature of 30° C. to 48° C. The EMS energy has an output voltage of 20 V to 30 V, a maximum current of 10 mA to 30 mA, a pulse width of 20 us to 500 us, and a frequency of 2 Hz to 500 Hz. In addition, the electrode unit 140 may further have a human body sensing function or a contact temperature sensing function.

Since the RF energy or the EMS energy is generated in the above-mentioned range, the effect of treating the vagina may be further improved. The RF energy may generate frictional heat by allowing high-frequency current to penetrate into the muscles in the vagina. Specifically, the RF energy may stimulate and activate a dermal layer and a collagen layer inside the vagina to increase a temperature, thereby further improving the effect of the LEDs. In addition, the EMS energy may use micro-currents to gently stimulate skin and muscles in the vagina, enhance the skin and the muscles, and promote the formation of collagen.

In addition, the electrode unit 140 may further have the human body sensing function or the contact temperature sensing function, and the human body sensing may control whether the RF energy or the EMS energy is generated by the electrode unit 140. Specifically, the electrode unit 140 may operate the RF energy or the EMS energy when the skin is sensed by the human body sensing. In addition, the electrode unit may control the operation of the RF energy or the EMS energy by the contact temperature sensing function. The temperature of the skin in the vagina may be raised by the electrode unit 140, and the contact temperature sensing function may stop the operation of the electrode unit 140 when the temperature of the skin is raised to a predetermined range or higher. A control unit may be provided in the housing part 300 to be described below, and the control unit may control one or more of the first LED units 120, the electrode units 140, and the second LED units 130.

The handle part 200 may include a power button 210 configured to turn on/off a power source of the battery, and a level button 220 configured to control intensity of one or more of the first LED units 120, the electrode units 140, and the second LED units 130.

In addition, the handle part 200 may further have a charge state display unit 230 including LEDs to check a state of charge of the battery embedded in the handle part 200, and a USB terminal electrically connected to the embedded battery. The handle part 200 is inserted into the housing part 300, and the battery may be charged with power supplied through the housing part 300. In addition, the battery may be charged selectively through the USB terminal provided in the handle part 200, and the state of charge (SOC) of the battery may be displayed on the charge state display unit 230. As described above, the vaginal treatment device 10 according to the present exemplary embodiment is provided in the form of the hand piece 20, and the hand piece 20 may be operated in a wireless manner by the embedded battery. In addition, the battery in the handle part 200 of the hand piece 20 may be charged through the USB terminal provided in the handle part 200 or charged through the housing part 300, and the state of charge of the battery may be checked by the charge state display unit 230. Therefore, the vaginal treatment device 10 may easily check the state of charge of the battery without requiring an electric wire or the like for supplying power, and as a result, there is an advantage in that the user may more conveniently use the vaginal treatment device 10.

The housing part 300 may include a bottom housing 310 having an internal space 350 for receiving the main body part 100 and at least a part of the handle part 200, and a top housing 320 provided to cover one side of the bottom housing 310 and configured to cover the handle part 200.

The bottom housing 310 may further include a USB PCB terminal 330 configured to be supplied with power from the outside, and a terminal plate 340 configured to be electrically connected to the handle part 200.

The terminal plate 340 may be electrically connected to terminal blocks 240 provided on the handle part 200, and the battery in the handle part 200 may be charged through the terminal blocks 240.

For example, the terminal plate 340 is provided at an outer circumferential edge of an upper receiving portion 352, and at least a part of an outer surface of the handle part 200 is seated at the outer circumferential edge of the upper receiving portion 352, such that the terminal blocks 240 of the handle part 200 and the terminal plate 340 may be in contact with each other and electrically connected to one another.

The internal space 350 of the housing part 300 may be provided in the bottom housing 310. The internal space 350 may include a lower receiving portion 351 provided to correspond to the main body part 100 and disposed at a lower side of the housing part 300 so that the main body part 100 is inserted into the lower receiving portion 351, and the upper receiving portion 352 connected to an upper side of the lower receiving portion 351 and configured to receive at least a part of the handle part 200.

A part of the handle part 200 may be inserted into the upper receiving portion 352, whereas the other part of the handle part 200 may protrude upward from the bottom housing 310. In addition, the top housing 320 may be provided in a dome shape so as to surround the handle part 200 protruding through the bottom housing 310 and may cover the handle part 200 protruding upward from the bottom housing 310. One or more reinforcing ribs 321 may be provided on an inner surface of the top housing 320 so as to reinforce strength of the top housing 320.

Hereinafter, another exemplary embodiment of the present disclosure will be described with reference to FIGS. 11A to 16. Because the configurations, except for the configurations to be described below, are similar to the configurations disclosed in the exemplary embodiment described with reference to FIGS. 1 to 10, a detailed description thereof will be omitted.

Figure 11A:
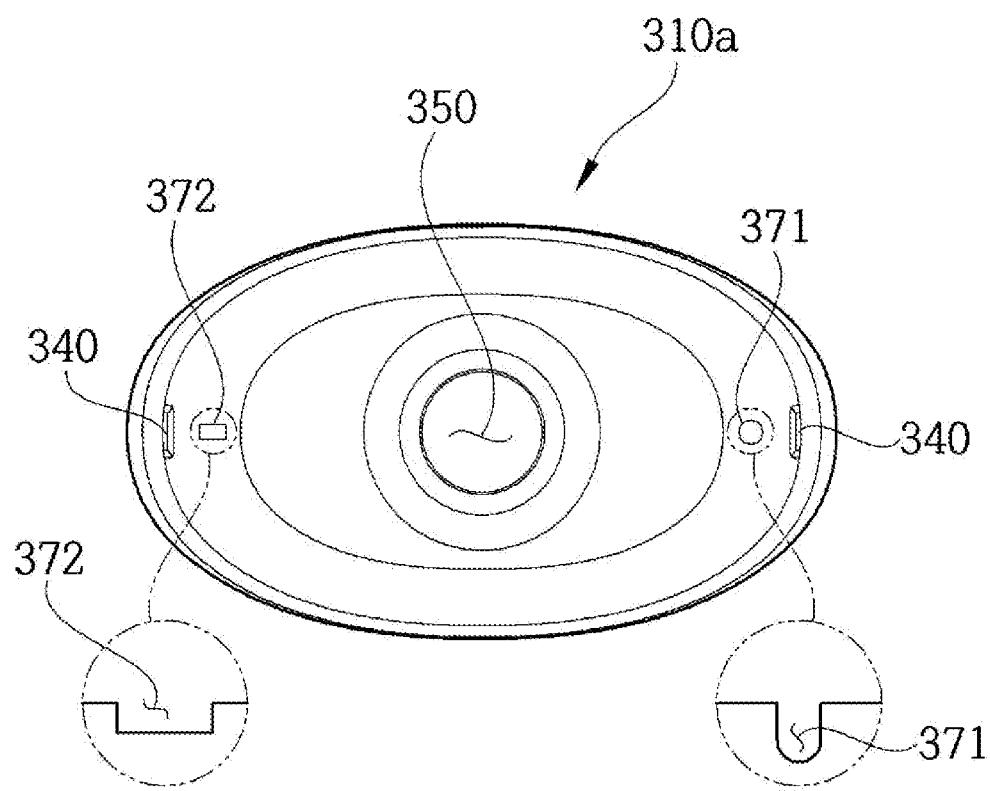
FIGS. 11A and 11B are views illustrating a bottom housing and a hand piece according to another exemplary embodiment of the present disclosure.
Figure 11B:
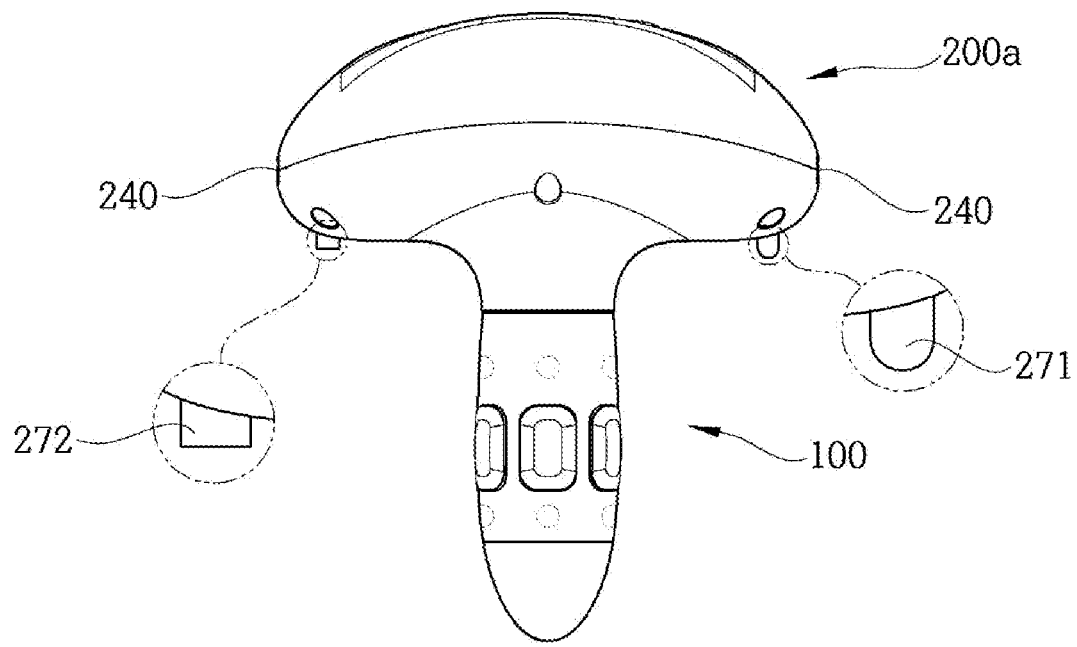

FIGS. 11A and 11B are views illustrating a bottom housing and a hand piece according to another exemplary embodiment of the present disclosure.

Referring to FIGS. 11A and 11B, in a vaginal treatment device according to the present exemplary embodiment, first and second protruding key portions 271 and 272 and first and second key groove portions 371 and 372 may be provided on a handle part 200a and a housing part, respectively, in order to guide the handle part 200a to a position at which the handle part 200a is inserted into the internal space 350 of the housing part.

After the handle part 200a is inserted into the housing part, an upper surface of the handle part 200a may be exposed, and a lower surface of the handle part 200a, which is opposite to the upper surface, may be inserted into the internal space 350 of the housing part. The internal space 350 is provided in a bottom housing 310a of the housing part, and the internal space 350 includes a lower receiving portion into which the main body part 100 is inserted, and an upper receiving portion into which a lower side of the handle part 200a is inserted. The lower receiving portion and the upper receiving portion may be provided to communicate with each other.

The first protruding key portion 271 and the second protruding key portion 272 may be provided on the lower surface of the handle part 200a so as to protrude from the lower surface of the handle part 200a and disposed at positions corresponding to an outer circumferential edge of the upper receiving portion. The main body part 100 may be connected to an approximately central portion of the lower surface of the handle part 200a, and the first protruding key portion 271 and the second protruding key portion 272 may be provided at the positions corresponding to one side and the other side of the handle part 200a with the main body part 100 interposed therebetween.

Terminal blocks provided in the handle part 200a may include a first terminal block 241, which is a (+) terminal, and a second terminal block 242, which is a (−) terminal, and the first terminal block 241 and the second terminal block 242 may be provided to be spaced apart from each other. The first protruding key portion 271 may be provided adjacent to the first terminal block 241, and the second protruding key portion 271 may be provided adjacent to the second terminal block 242.

The first and second key groove portions 371 and 372 may be provided in the upper receiving portion and formed to be concave inward corresponding to the first and second protruding key portions 271 and 272 so that the first and second protruding key portions 271 and 272 are inserted into the first and second key groove portions 371 and 372, respectively. The first and second protruding key portions 271 and 272 may have different shapes. For example, the first protruding key portion 271 may be provided in a cylindrical shape having a circular transverse section, and the second protruding key portion 272 may be provided in a plate shape having a "–" shaped transverse section.

In the present exemplary embodiment, the first protruding key portion 271 may have a cylindrical shape, and the second protruding key portion 271 may protrude in a plate shape. Therefore, when the main body part 100 and the handle part 200a are inserted into the internal space 350 of the housing part such that the first and second terminal blocks 241 and 242 of the handle part 200a and the terminal plate 340 are electrically connected, the first and second protruding key portions 271 and 272, which have different shapes, may easily guide the first and second terminal blocks 241 and 242 so that the first and second terminal blocks 241 and 242 correspond to the (+) terminal and the (−) terminal of the terminal plate 340.

For example, since the first and second protruding key portions 271 and 272 are provided to protrude downward from the lower surface of the handle part 200a, the first and second protruding key portions 271 and 272 cannot be inserted into the first and second key groove portions 371 and 372 when the (+) and (−) terminals of the first and second terminal blocks 241 and 242 of the handle part 200a do not correspond to the (+) and (−) terminals of the terminal plate 340. As a result, it is possible to prevent an electrical problem caused by erroneous contact between the (+) and (−) terminals.

Figure 12:
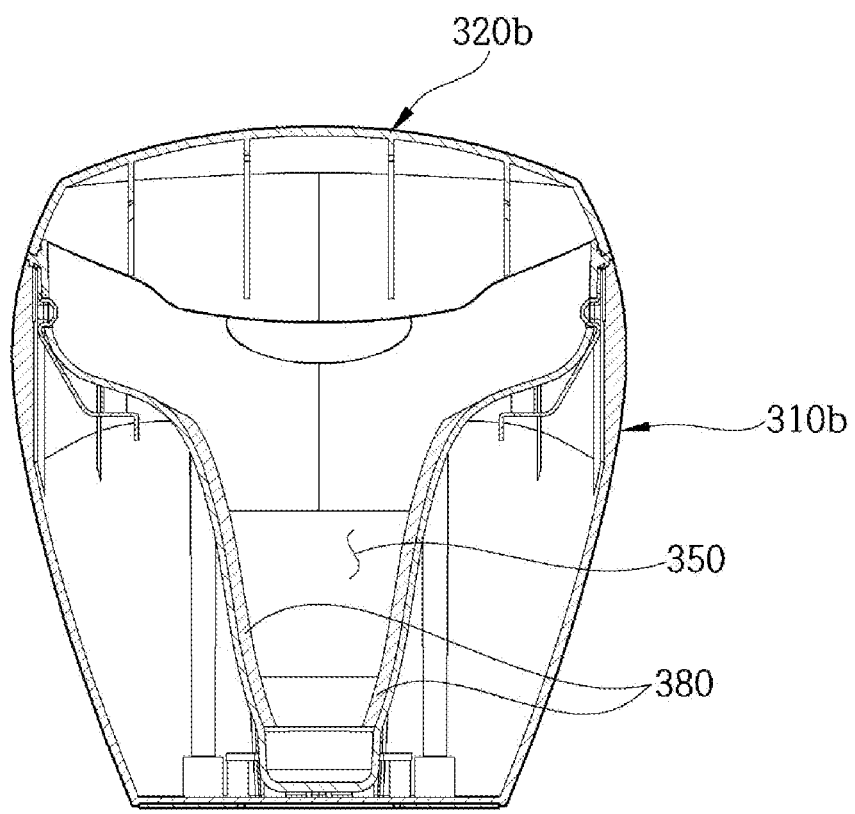
FIG. 12 is a view illustrating a bottom housing according to still another exemplary embodiment of the present disclosure.

FIG. 12 is a view illustrating a bottom housing according to still another exemplary embodiment of the present disclosure.

Referring to FIG. 12, in a vaginal treatment device according to the present exemplary embodiment, a housing part 300b may include a bottom housing 310b having an internal space 350, and a top housing 320b configured to cover one side of the bottom housing 310b.

The bottom housing 310b may further have planar heating elements 380 provided at positions corresponding to the outer circumferential edge of the internal space 350 in order to dry or sterilize the main body part received in the internal space 350. The planar heating element 380 may be made by attaching coating paper to two surfaces of sun-paper heating sheets, which are made of carbon fiber heating paper, between the sun-paper heating sheets and configured to emit heat by supplying power to two electrodes.

The main body part is inserted and stored in the housing part 300b after foreign substances on the outer surface of the main body part are removed by washing the main body part with water or using cleaning tissue after use. In this case, the main body part may be inserted into the internal space 350 of the bottom housing 310b, and the main body part may be sterilized and dried by the planar heating element 380. Therefore, it is possible to prevent a problem with bacteria or the like that may occur while the hand piece including the main body part and the handle part is stored, and as a result, it is possible to use the vaginal treatment device more cleanly.

The planar heating element 380 may include a sun-paper heating sheet made of carbon fiber heating paper, a pair of electrode bodies disposed on one surface of the carbon fiber sun-paper heating sheet so as to be spaced apart from each other and configured to apply electricity to the carbon fiber sun-paper heating sheet through a power line, and coating films configured to surround and support the sun-paper heating sheet and the pair of electrode bodies from the outside, the coating films being made of a PVC material and applied to upper and lower surfaces of an insulation member having joint portions tightly compressed to each other.

Figure 13:
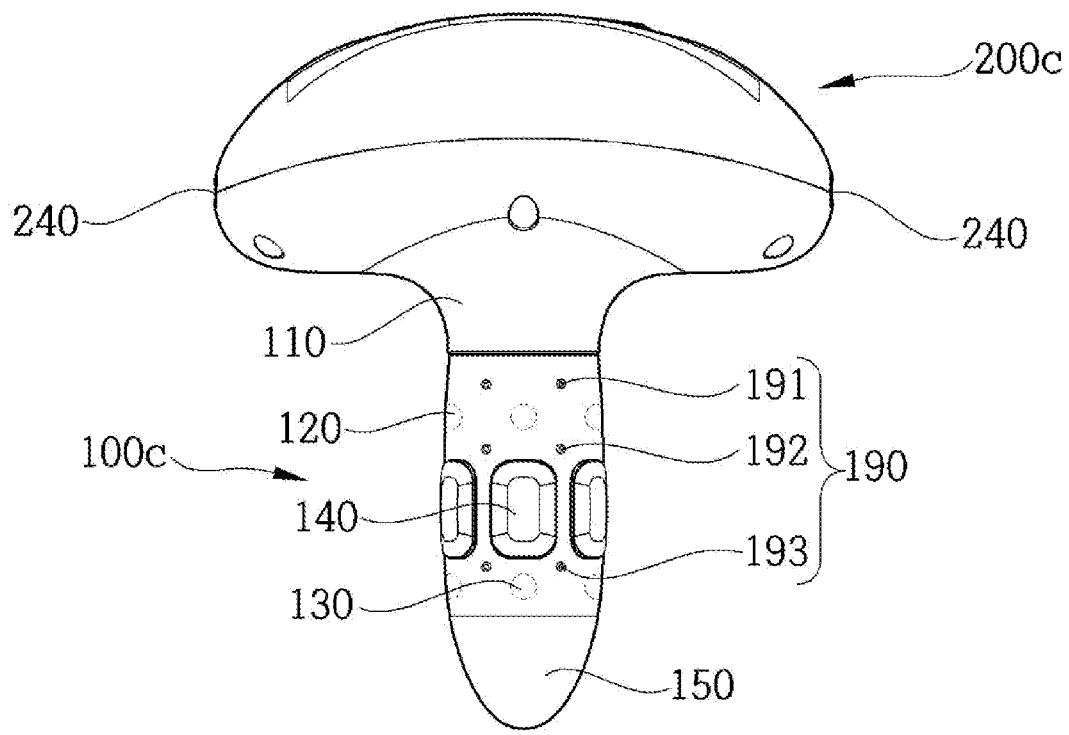
FIG. 13 is a view illustrating a hand piece according to yet another exemplary embodiment of the present disclosure.

FIG. 13 is a view illustrating a hand piece according to yet another exemplary embodiment of the present disclosure.

Referring to FIG. 13, in a vaginal treatment device according to the present exemplary embodiment, a main body part 100c may further have human body detecting sensors 190. When power is applied through the handle part 200c, the LED irradiation units 120 and 130 or the electrode units 140 may be operated when the sensors 190 detect a human body. The LED irradiation units 120 and 130 may include the first LED units 120 including red-light LEDs, and the second LED units 130 including blue-light LEDs.

The first LED units 120, the electrode units 140, and the second LED units 130 may be sequentially aligned and spaced apart from one another on the main body part 100c. The sensors 190 may include first sensors 191 provided between the first LED units 10 and the electrode units 140 to control the operations of the first LED units 120, second sensors 192 provided between the electrode units 140 and the second LED units 130 to control the operations of the electrode units 140, and third sensors 193 provided between the second LED units 130 and the end of the main body part 100c to control the operations of the second LED units 130.

The first LED units 120, the electrode units 140, and the second LED units 130 are provided to operate when the human body is sensed by the first to third sensors 191, 192, and 193.

Therefore, since the first LED units 120, the electrode units 140, and the second LED units 130 are operated after the first LED units 120, the electrode units 140, and the second LED units 130 are positioned at predetermined positions, it is possible to prevent the light or the RF energy from being transferred to an undesired portion, and as a result, it is possible to more efficiently control the first LED units 120, the electrode units 140, and the second LED units 130 so that the first LED units 120, the electrode units 140, and the second LED units 130 are operated in the vagina.

Figure 14:
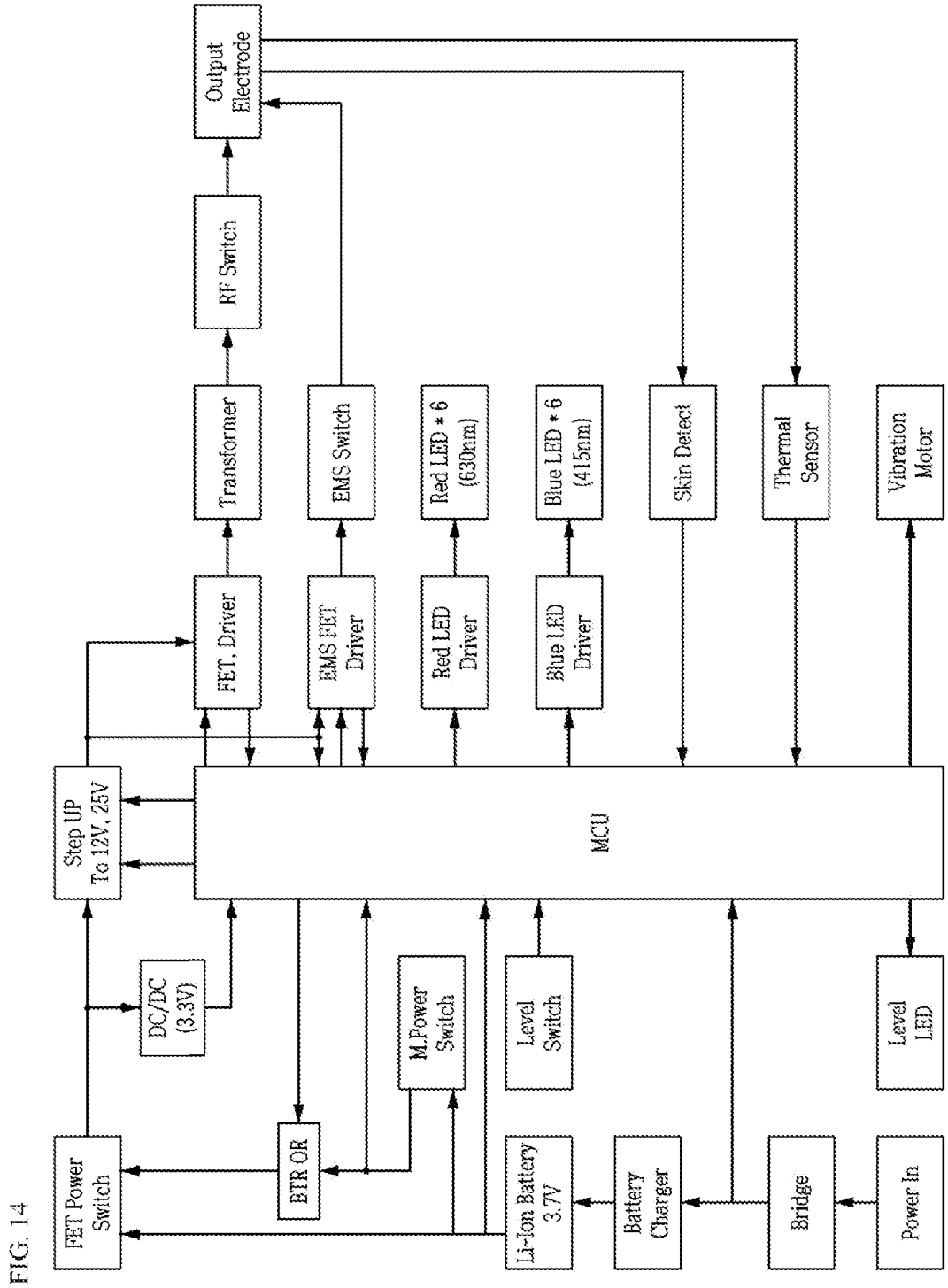
FIG. 14 is a schematic flowchart illustrating a system of the vaginal treatment device according to the present disclosure.
Figure 15:
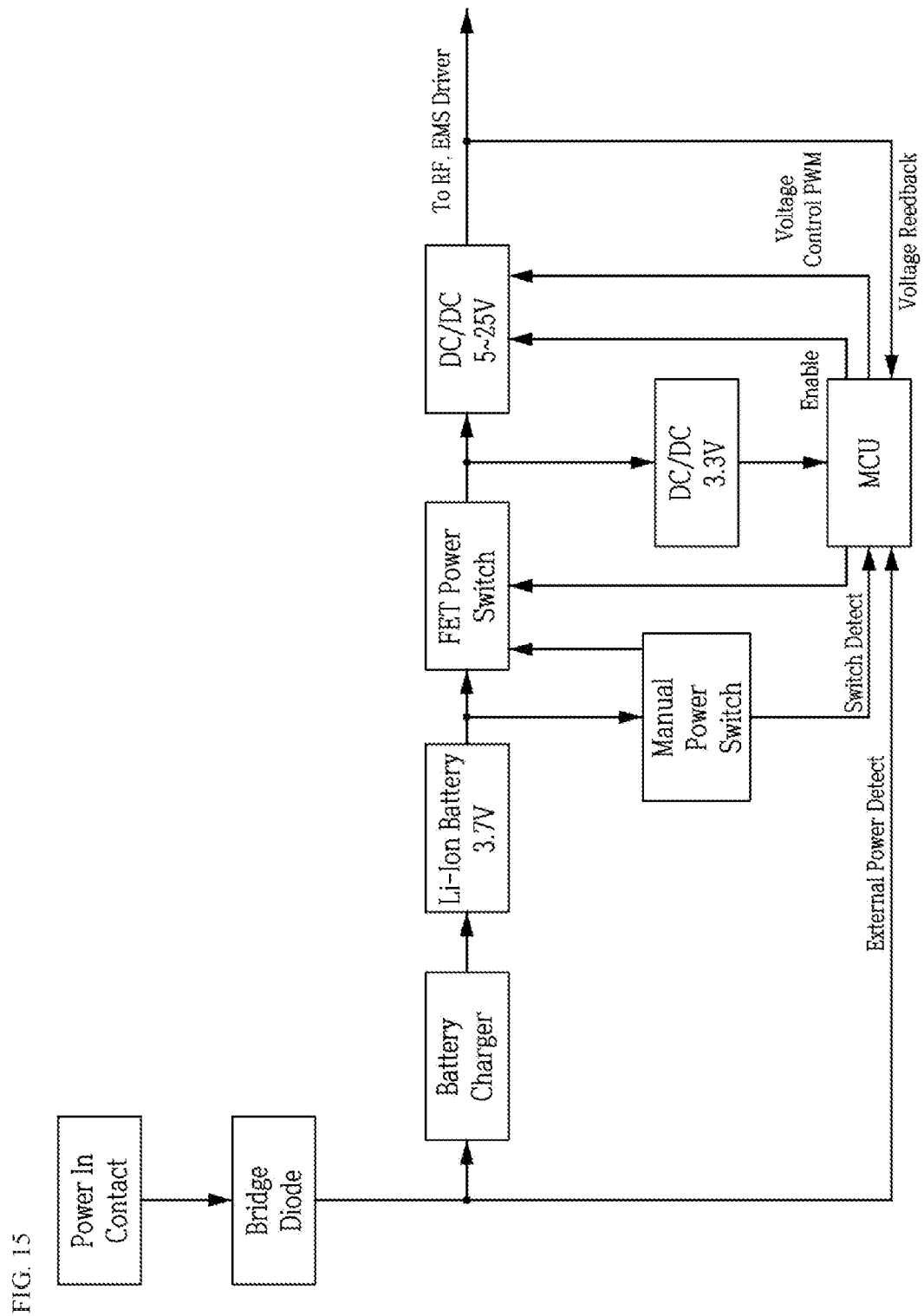
FIG. 15 is a view illustrating a configuration of a power source of the vaginal treatment device according to the present disclosure.
Figure 16:
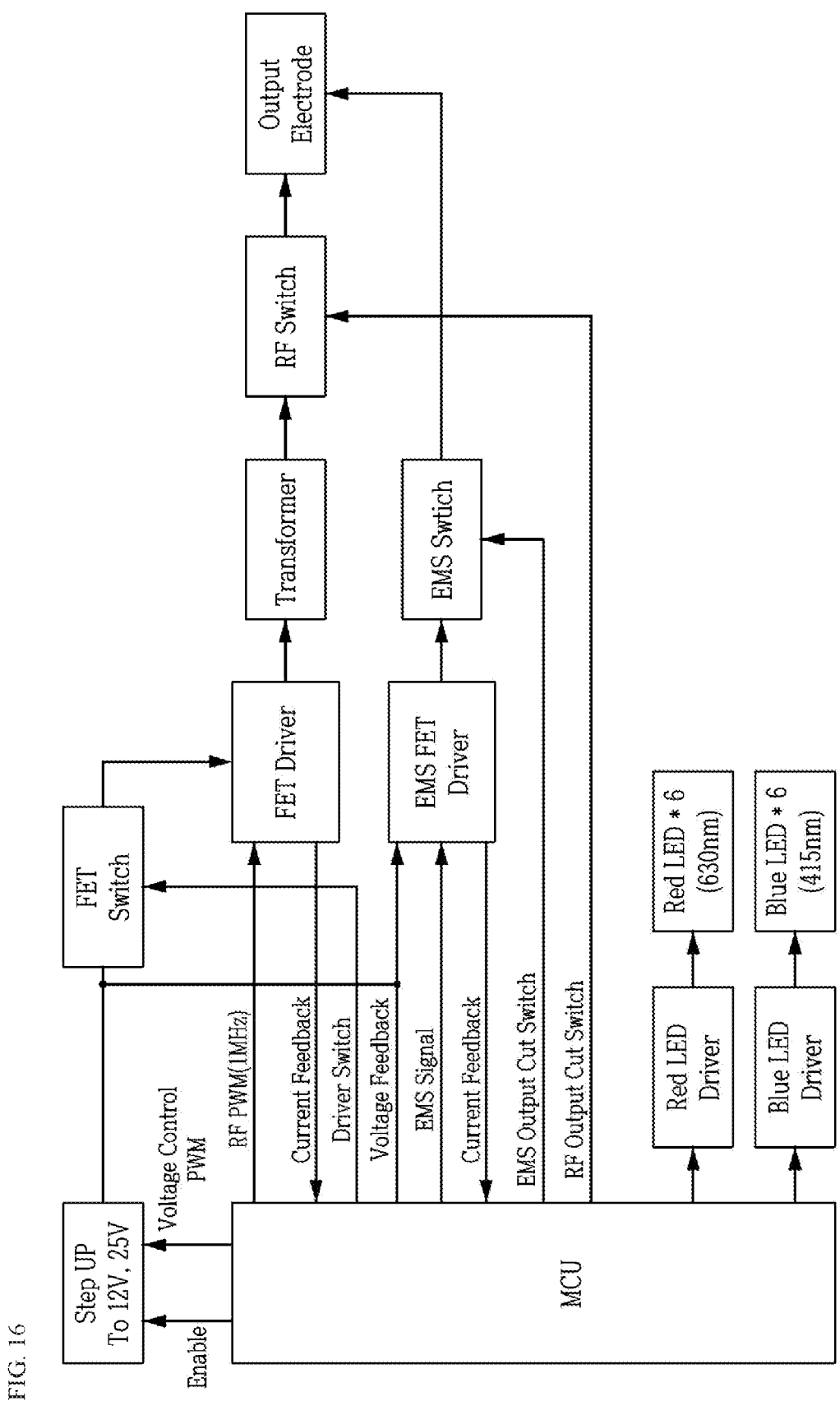
FIG. 16 is a view illustrating an output configuration of the vaginal treatment device according to the present disclosure.

FIG. 14 is a schematic flowchart illustrating a system of the vaginal treatment device according to the present disclosure. FIG. 15 is a view illustrating a configuration of a power source of the vaginal treatment device according to the present disclosure. FIG. 16 is a view illustrating an output configuration of the vaginal treatment device according to the present disclosure.

Referring to FIGS. 14 to 16, the vaginal treatment device according to the present exemplary embodiment may use the control unit (MCU) to control the operations of the LED units and the electrode units and control a degree to which the battery provided in the handle part is charged or discharged. In addition, the electrode units may generate the RF energy and the EMS energy, or the electrode units may be controlled by the control unit so as to generate only one of the RF energy and the EMS energy without generating both the RF energy and the EMS energy.

It may be understood by a person skilled in the art that the present disclosure may be carried out in other specific forms without changing the technical spirit or the essential characteristics of the present disclosure. Therefore, it should be understood that the above-described exemplary embodiments are illustrative in all aspects and do not limit the present disclosure. The scope of the present disclosure is represented by the claims to be described below rather than the detailed description, and it should be interpreted that all the changes or modified forms, which are derived from the meaning and the scope of the claims and the equivalents thereto, are included in the scope of the present disclosure.

What is claimed is:

1. A vaginal treatment device using LEDs, radio frequency (RF) electromagnetic waves, and electro muscular stimulation (EMS), the vaginal treatment device comprising:
    a main body part configured to be inserted into a vagina and having one or more LED irradiation units configured to irradiate an interior of the vagina with light, and electrode units configured to transfer radio frequency (RF) energy or electro muscular stimulation (EMS) energy into the vagina;
    a handle part embedded with a battery and electrically connected to one end of the main body part and configured to control transmission and reception to/from the LED irradiation units or the electrode units; and
    a housing part electrically connected to the handle part and configured to charge the battery;
    wherein the LED irradiation units comprise first LED units comprising red-light LEDs, and second LED units comprising blue-light LEDs, and wherein the first LED units, the electrode units, and the second LED units are sequentially provided and aligned on the main body part;
    wherein the main body part extends in a first direction, the handle part is provided on the main body part and extends perpendicular to the first direction, and the first LED unit is provided adjacent to the handle part.

2. The vaginal treatment device of claim 1, wherein the first LED unit is spaced apart from one end of the main body part by 25 mm to 35 mm, and the second LED unit is spaced apart from one end of the main body part by 55 mm to 65 mm.

3. The vaginal treatment device of claim 1, wherein the main body part further comprises a silicone cover configured to cover at least some of the LED irradiation units, and the electrode units are provided on an outer surface of the silicone cover.

4. The vaginal treatment device of claim 1, wherein the first LED unit emits light in a red wavelength band of 575 nm to 750 nm, and the second LED unit emits light in a blue wavelength band of 405 nm to 520 nm.

5. The vaginal treatment device of claim 4, wherein the electrode unit is spaced apart from one end of the main body part by 40 mm to 50 mm, the RF energy has an output power of 10 W to 20 W, an output voltage of 150 Vpp to 200 Vpp, a frequency of 0.8 MHz to 1.5 MHz, and a temperature of 30° C. to 48° C., and the EMS energy has an output voltage of 20 V to 30 V, a maximum current of 10 mA to 30 mA, a pulse width of 20 us to 500 us, and a frequency of 2 Hz to 500 Hz.

6. The vaginal treatment device of claim 1, wherein the housing part comprises:
    a bottom housing having an internal space for receiving the main body part and at least a part of the handle part, and a top housing provided to cover one side of the bottom housing and configured to cover the handle part.

7. The vaginal treatment device of claim 6, wherein the bottom housing further comprises:
    a USB PCB terminal configured to be supplied with power from the outside; and
    a terminal plate configured to be electrically connected to the handle part,
    wherein the handle part has terminal blocks configured to be electrically connected to the terminal plate,
    wherein the internal space comprises:
    a lower receiving portion provided to correspond to the main body part and disposed at a lower side of the housing part so that the main body part is inserted into the lower receiving portion; and
    an upper receiving portion connected to an upper side of the lower receiving portion and configured to receive at least a part of the handle part,
    wherein one part of the handle part is inserted into the upper receiving portion, and the other part of the handle part protrudes upward from the bottom housing,
    wherein the top housing is provided in a dome shape so as to surround the handle part and cover the handle part protruding upward from the bottom housing, and
    wherein one or more reinforcing ribs are provided on an inner surface of the top housing so as to reinforce strength of the top housing.

8. The vaginal treatment device of claim 7, wherein the bottom housing further has planar heating elements provided at positions corresponding to an outer circumferential edge of the internal space in order to dry or sterilize the main body part received in the internal space, and
    wherein the planar heating element is made by attaching coating paper to two surfaces of sun-paper heating sheets, which are made of carbon fiber heating paper, between the sun-paper heating sheets and configured to emit heat by supplying power to two electrodes.

9. The vaginal treatment device of claim 6, wherein the terminal plate is provided at an outer circumferential edge of the upper receiving portion, at least a part of an outer surface of the handle part is seated at the outer circumferential edge of the upper receiving portion, and the terminal blocks of the handle part and the terminal plate are connected to one another.

10. The vaginal treatment device of claim 9, wherein a first protruding key portion and a second protruding key portion are provided on a lower surface of the handle part so as to protrude from the lower surface of the handle part and disposed at positions corresponding to the outer circumferential edge of the upper receiving portion,
    wherein the terminal blocks comprise a first terminal block, which is a (+) terminal, and a second terminal block, which is a (−) terminal, and the first terminal block and the second terminal block are provided to be spaced apart from each other,
    wherein the first protruding key portion is provided adjacent to the first terminal block, and the second protruding key portion is provided adjacent to the second terminal block, and
    wherein first and second key groove portions are provided in the upper receiving portion and formed to be concave inward corresponding to the first and second protruding key portions so that the first and second protruding key portions are inserted into the first and second key groove portions, respectively.

11. The vaginal treatment device of claim 10, wherein the first protruding key portion is provided in a cylindrical shape having a circular transverse section, and the second protruding key portion is provided in a plate shape having a "-" shaped transverse section.

12. The vaginal treatment device of claim 1, wherein the electrode unit further has a human body sensing function or a contact temperature sensing function.

13. The vaginal treatment device of claim 1, wherein the main body part further has human body detecting sensors,
wherein when power is applied through the handle part, the LED irradiation units or the electrode units are operated after the sensors detect a human body,
wherein the LED irradiation units comprise:
the first LED units comprising red-light LEDs; and
the second LED units comprising blue-light LEDs,
wherein the first LED units, the electrode units, and the second LED units are sequentially disposed on the main body part, and
wherein the sensors comprise:
first sensors provided between the first LED units and the electrode units to control operations of the first LED units;
second sensors provided between the electrode units and the second LED units to control operations of the electrode units; and
third sensors provided between the second LED units and an end of the main body part to control operations of the second LED units.

14. The vaginal treatment device of claim 1, wherein the main body part and the handle part are integrally provided,
wherein the handle part in which the battery is embedded is configured to operate the LED irradiation units and the electrode units of the main body part in a wireless manner,
wherein the main body part extends from one end in a first direction and has an end,
wherein the handle part is connected to one end of the main body part so as to be perpendicular to one end of the main body part, and cross sections of the main body part and the handle part are connected in a T shape,
wherein the main body part has a silicone cover provided at the end of the main body part and configured to cover the LED irradiation units of the main body part,
wherein the main body part has a body integrally connected to the handle part and having a lower end having a flat surface, and the silicone cover configured to cover the lower end of the body,
wherein the LED irradiation units are mounted on the body,
wherein the silicone cover has a cone shape, and an interior at an end of the silicone cover is provided to be in contact with the lower end of the body, and
wherein an outer surface of the silicone cover is rounded without edge.

15. The vaginal treatment device of claim 14, wherein the LED irradiation units comprise:
the first LED units comprising red-light LEDs; and
the second LED units comprising blue-light LEDs;
wherein the first LED units, the electrode units, and the second LED units are sequentially provided and aligned at one end of the main body part,
wherein the first LED units and the second LED units are provided inside the silicone cover and covered by the silicone cover,
wherein the plurality of electrode units is provided on the outer surface of the silicone cover so as to have a quadrangular cross section, and
wherein an outer surface of the electrode unit is rounded in the first direction.

16. The vaginal treatment device of claim 15, wherein the plurality of electrode units are disposed in a direction perpendicular to the first direction so as to surround the main body part and provided to be spaced apart from one another, and
wherein the handle part comprises:
a power button configured to turn on/off a power source of the battery; and
a level button configured to control intensity of one or more of the first LED units, the electrode units, and the second LED units.

* * * * *